United States Patent [19]

Wagner

[11] Patent Number: 5,017,473
[45] Date of Patent: May 21, 1991

[54] HOMOGENEOUS CHEMILUMINESCENCE IMMUNOASSAY USING A LIGHT ABSORBING MATERIAL

[75] Inventor: Daniel B. Wagner, Raleigh, N.C.

[73] Assignee: Becton, Dickinson and Company, Franklin Lakes, N.J.

[21] Appl. No.: 54,466

[22] Filed: May 26, 1987

[51] Int. Cl.$^5$ .................... G01N 33/53; G01N 21/76; G01N 33/543; C12Q 1/28

[52] U.S. Cl. ................................. 435/7.92; 435/28; 435/810; 435/7.93; 435/975; 436/172; 436/518; 436/808; 436/810; 436/826

[58] Field of Search .............................. 435/7, 810, 28; 436/501, 518, 524, 526, 172, 826, 808, 810

[56] References Cited

U.S. PATENT DOCUMENTS 4,614,712 9/1986 Baldwin et al. .......................... 435/4
4,731,337 3/1988 Luotola et al. ...................... 436/526

Primary Examiner—Esther L. Kepplinger
Assistant Examiner—Janelle Graeter
Attorney, Agent, or Firm—Richard E. Brown

[57] ABSTRACT

A method for separation-free solid phase immunoassay of an analyte includes contacting an antianalyte attached to the surface of a solid support with the analyte, a light absorbing material and a tracer for the analyte which includes a label. The resulting mixture is incubated and chemiluminescence is generated. All of the chemiluminescence is absorbed by the light absorbing material except that associated with the bound tracer whereby the only emission detected is due to the bound tracer. Since emission from free tracer in the fluid phase of the assay medium is not detected, separation of the bound and free fractions is unnecessary. The invention includes a kit of materials useful in performing an immunoassay in accordance with the method of the invention.

18 Claims, 1 Drawing Sheet

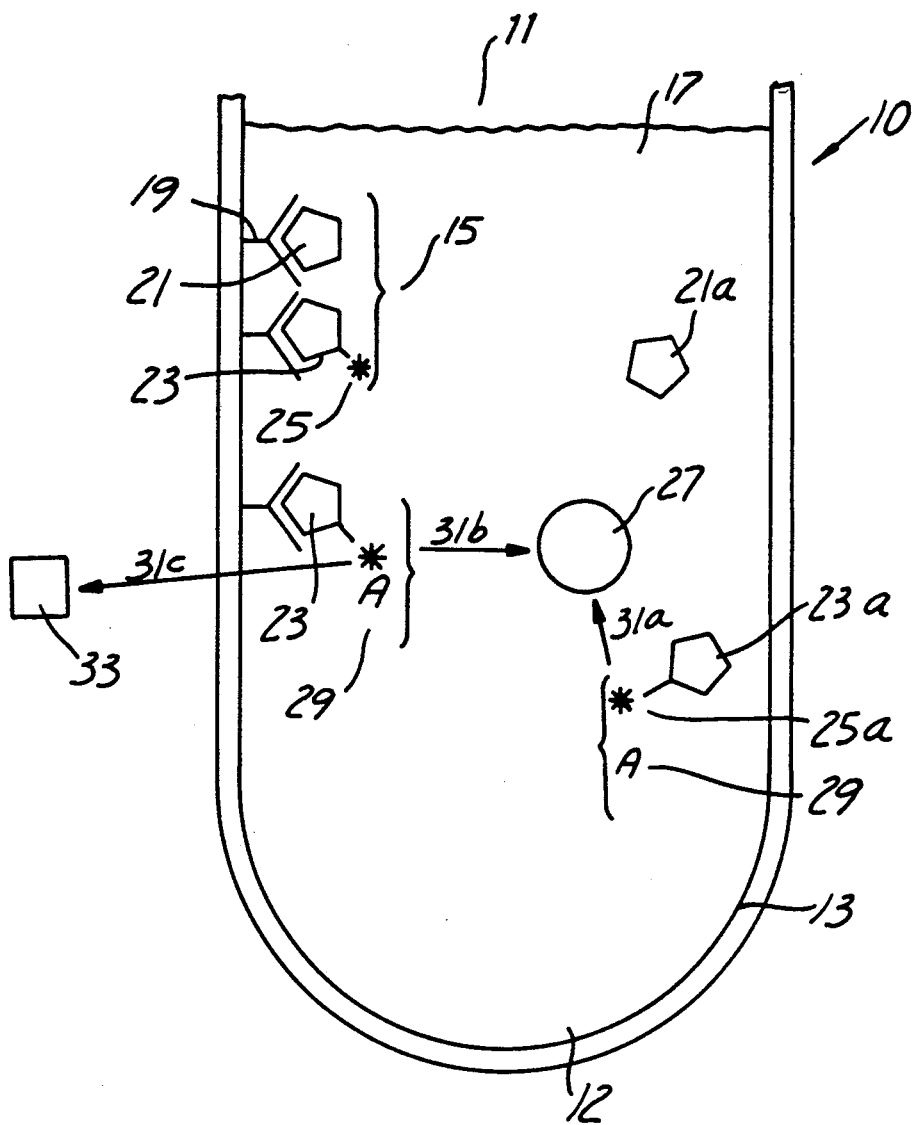
Figure

HOMOGENEOUS CHEMILUMINESCENCE IMMUNOASSAY USING A LIGHT ABSORBING MATERIAL

BACKGROUND OF THE INVENTION

1. Field of the Invention

This invention relates to an immunoassay of an analyte and materials used therein, and more particularly relates to a method and materials for immunoassay which does not require separation of bound and free fractions.

2. Description of the Prior Art

A variety of assay systems which are both rapid and sensitive has been developed to determine the concentration of a substance in a fluid. Immunoassays depend on the binding of an antigen or hapten to a specific antibody and have been particularly useful because they give high levels of specificity and sensitivity. These assays generally employ the antigen in labeled form, the labeled antigen often being referred to as the tracer. Immunoassay procedures may be carried out in solution or on a solid support and may be either heterogeneous or homogeneous. Heterogeneous assays require a separation of bound tracer from free (unbound) tracer. Homogeneous assays do not require a separation step and thereby provide significant advantage in speed, convenience and ease of automation over heterogeneous assays.

Radioimmunoassay (RIA) procedures use radioisotopes as labels, provide high levels of sensitivity and reproducibility, and are amenable to automation for rapid processing of large numbers of samples. However, all RIA procedures require a separation step, since the parameter measured (nuclear decay) cannot be controlled by changing assay conditions or components. In addition, isotopes are costly, have relatively short shelf lives, require expensive and complex equipment, and extensive safety measures for their handling and disposal must be followed.

Enzymes have also been used as labels in immunoassay. Enzymeimmunoassay (EIA) may be homogeneous and does not require precautions against radioactivity. Conjugation of an enzyme with a protein is usually straightforward, and the resulting protein-enzyme conjugate is generally stable. However, EIA depends on the reaction of the enzyme conjugate with a substrate to produce a color which is measured, and thus requires the additional step of providing an enzyme substrate. In addition, sufficient time must be allowed for color development and an expensive spectrophotometer for measuring color change must be provided.

Some of the above disadvantages associated with RIA or EIA have been overcome by use of fluorochromes as labels in immunoassay. Fluoroimmunoassay (FIA) provides direct detection of the label and is readily adaptable to homogeneous assay procedures. However, known homogeneous FIA methods using organic fluorochromes, such as fluorescein or rhodamine derivatives, have not achieved the high sensitivity of RIA or EIA, largely because of light scattering by impurities suspended in the assay medium and by background fluorescence emission from other fluorescent materials present in the assay medium.

The development of time-resolved fluoroimmunoassay (TR-FIA) has contributed to overcoming these problems, however, FIA methods in general require complex instrumentation to provide the incident radiation and separate it from the fluorescence emission to be measured.

Other immunoassay procedures have been developed in which the label is chemiluminescent. In chemiluminescence immunoassay (CIA), light is produced by a chemical reaction and external incident radiation is not required. U.S. Pat. No. 4,104,029 to Maier discloses CIA in which the chemiluminescence, preferably from luminol, is measured directly. U.S. Pat. No. 4,375,972 to Forgione, et al. discloses catalysis of luminol chemiluminescence by a metallo-porphyrin. In U.S. Pat. No. 4,238,195 to Boguslaski et al. the chemiluminescence is absorbed by a fluorochrome present in the assay medium and is emitted and measured as fluorescence emission. U.S. Pat, No. 4,372,745 to Mandle et al. discloses encapsulation of a fluorochrome, conjugation of the encapsulated fluorochrome to a component of an immunological reaction, and disruption of the capsule to free the fluorochrome prior to activation of the chemiluminescent reaction.

CIA and EIA are combined in U.S. Pat. No. 4,302,534 to Halmann et al. An enzyme conjugated to a component of an immunological reaction reacts with a substrate to produce light which is measured. In U.S. Pat. No. 4,492,751 to Boguslaski et al., the enzyme substrate rather than the enzyme is conjugated to the immunological component.

In U.S. Pat. No. 4,220,450 to Maggio, a chemiluminescent agent conjugated to a ligand and a quenching agent conjugated to an antiligand are brought into sufficiently close proximity by immunological binding that emission from the bound chemiluminescent agent is energy-transferred to the quenching agent and thereby modulated in a detectable way, as, for example, by signal reduction resulting from radiationless decay, or emission at a different wavelength.

Although the above methods have improved immunoassay, there is still a need for a procedure affording high sensitivity which can be carried out rapidly without requiring a separation of bound and free fractions.

SUMMARY OF THE INVENTION

One aspect of the present invention comprises a method for solid phase immunoassay of an analyte without separation of bound and free fractions. An antianalyte attached to the surface of a solid support is contacted with a fluid sample containing the analyte, a light absorbing material and a tracer for the analyte having an attached label. After incubation of the assay mixture, chemiluminescence is induced and light emission associated with bound tracer is measured. The magnitude of light emission is compared with the magnitude of light emission measured when one or more known quantities of analyte is assayed under essentially identical conditions.

The label is preferably one of the components of the chemiluminescence source, and the light absorbing material preferably has an absorption band which overlaps the band of chemiluminescence emission.

A competitive assay may be carried out in which the tracer and the analyte compete for an insufficient number of antianalyte binding sites. Alternatively, the assay may be performed in a sandwich mode in which substantially all of the analyte binds to both the antianalyte and the tracer.

Another aspect of the invention includes a kit of materials for performing the method of the invention.

In accordance with the method of the invention, a solid phase CIA is carried out which does not require a separation of bound and unbound fractions whereby operational simplicity, speed and convenience are achieved. The method of the invention provides a highly sensitive homogeneous assay essentially free of interfering emission from other materials whereby an analyte present in very low concentration can be accurately determined. Because the procedure is exceptionally facile to carry out, it is readily adaptable to automation.

BRIEF DESCRIPTION OF THE DRAWINGS

The Figure shows a schematic representation of a tube and other components of use in a competitive immunoassay in accordance with the method of the invention.

DETAILED DESCRIPTION

While this invention is satisfied by embodiments in many different forms, there will herein be described in detail preferred embodiments of the invention, with the understanding that the present disclosure is to be considered as exemplary of the principles of the invention and is not intended to limit the invention to the embodiments illustrated. The scope of the invention will be measured by the appended claims and their equivalents.

In accordance with the method of the invention, the concentration of a substance present in a fluid sample may be determined by means of an immunological reaction. The substance, hereinafter referred to as the analyte, may be an antigen, a hapten or an antibody, and may be present in any suitable fluid. For example, the fluid may be a buffer, saline, or a body fluid such as serum or urine. In some cases, the analyte may be isolated from a body fluid and subsequently be introduced into a different fluid, such as buffer, for determination.

By the term "immunological reaction," as used herein, is meant a specific binding reaction of an antigen and an antibody, a hapten and an antibody, or any appropriate analogue of an antigen, an antibody, or a hapten which also binds specifically.

The immunological reaction of the method of the invention is carried out on the surface of a solid support. As known in the art, the solid support may be any support which does not interfere with the assay. Exemplary of solid supports which may be used are glass and polymeric materials, such as polyethylene, polystyrene and the like. Such supports may be fabricated into any suitable shape, such as sheets, plates, wells, or tubes.

An antianalyte is attached to the surface of the solid support. The antianalyte may be an antigen or an antibody which reacts specifically with the analyte, or it may be any appropriate analogue thereof which reacts specifically with the analyte. Attachment of the antianalyte to the solid support may be carried out by any conventional procedure, such as, for example, absorption or covalent bonding. These procedures are well known in the art, and no further details in these respects are deemed necessary for a complete understanding of the invention.

The quantity of antianalyte to be attached to the solid support depends on the type of assay to be carried out. In a competitive immunoassay as will first be described herein, a limited amount of antianalyte is attached, whereby insufficient binding sites are available and the analyte and a tracer for the analyte, described below, compete for the available sites. In a sandwich assay, as will subsequently be described, excess antianalyte is attached whereby essentially all analyte is bound to the antianalyte.

In a competitive assay in accordance with the method of the invention, the antianalyte attached to the solid support is contacted with a fluid containing an unknown quantity of analyte and a tracer for the analyte. The assay medium is incubated as described below to induce immunological reactions involving the analyte, the antianalyte and the tracer so that the assay medium contains free analyte, free tracer, bound analyte and bound tracer. If desired, the analyte and tracer may be added separately and two incubations carried out. Analyte and tracer bound to the antianalyte on the solid support are hereinafter referred to as the bound fraction, and analyte and tracer which do not bind to the antianalyte are hereinafter referred to as the free fraction.

Incubation may be carried out at any temperature and for any length of time suitable to facilitate the immunological reaction and thereby provide the aforementioned bound and free fractions. The incubation may be carried out, for example, at a temperature range from about 0° to 50° C., preferably from about 30° to 40° C., and may, but need not, result in equilibrium between these fractions.

The tracer provides a means to follow the course of the immunological reaction, and, in a competitive assay, preferably consists of a known quantity of the analyte or appropriate analogue thereof coupled to a component of the chemiluminescence source which serves as the label.

The chemiluminescence source may comprise any number of components which react to produce light. As mentioned above, one of the components is the label portion of the tracer. Another of the components necessary for the production of light, hereinafter referred to as the activator, may preferably be added subsequent to the immunological reaction.

In general, chemiluminescence sources may be divided into two classes, those including an enzyme component, and those which do not include an enzyme component. Both classes are fully described in the art, and the present invention is contemplated to cover both classes. Exemplary of enzyme-based systems are chemiluminescent sources in which light is produced from luciferin derivatives in the presence of luciferase, or systems in which light is produced by hydrogen peroxide and a 2,3-dihydro-1,4-phthalazindione, such as luminol, in the presence of a peroxidase, such as horseradish peroxidase. Exemplary of non-enzymatic systems are hydrogen peroxide with oxalyl chloride, oxamides or oxalyl diesters; luminol and alkaline hydrogen peroxide or an alkali hypochlorite; and bis acridinium salts, such as lucigenin, with alkaline hydrogen peroxide.

Any component of the source which can be attached to the analyte to provide the tracer may serve as the label. For example, an enzyme may be attached to the analyte and thus serve as the label portion of the tracer and a substrate for the enzyme present in the assay medium may serve as the activator. Conversely, the enzyme substrate may serve as the label, in which case the enzyme may be the activator. Alternatively, the label and the activator may both be non-enzymatic components of a chemiluminescence source.

The light absorbing material may be added to the assay system either before or after the immunological reaction, and may be any material which does not interfere with the immunological reaction and which has an absorption band whereby it may absorb the chemiluminescence. Suitable absorbing materials are selected depending on the label. Thus, for example, if the label is luminol, which may emit light at 400-450 nm, the light absorbing materials may be diazonium dyes such as Acid Yellow 29 (C.I. 18900) or Acid Yellow 99 (C.I. 13900), triphenylmethane dyes such as Xylenol Blue (Chemical Abstracts registry number 125-31-5), and any other material which absorbs strongly in the same part of the spectrum. If light is emitted in a different part of the spectrum (as may be the case when the luciferin-luciferase system is used), then the light absorbing material should absorb strongly at around 500 nm. This material may be a diazonium dye such as Acid Red 4 (C.I. 14710), an anthraquinone dye such as Carminic Acid (C.I. 75470), and the like. The concentration of the light-absorbing materials is determined by the absorbity of the dye and may be from about $10^{-2}$ to $10^{-6}$M.

The Figure shows assay system 10 to include a plastic, preferably polystyrene, tube 13 having an open end 11 and a closed end 12. Tube 13 contains a bound fraction 15 and fluid phase 17. Bound fraction 15 includes antianalyte 19 attached to the inside walls of tube 13 and bound analyte 21 and bound tracer 23. Bound tracer 23 comprises bound analyte 21 having attached thereto label 25. Fluid phase 17 includes free analyte 21a, free tracer 23a including label 25a, light absorbing material 27, and an activator of a chemiluminescence source, indicated by letter A and reference numeral 29. On reaction with labels 25 and 25a component 29 produces chemiluminescent light, schematically illustrated by reference lines 31a,b and c.

Light 31a generated by reaction of activator 29 and label 25a passes through fluid phase 17 and is absorbed by material 27. Light from bound tracer 23 includes emission 31b into fluid phase 17 where it is absorbed by material 27, and emission 31c outwardly through tube 13, which is preferably light transmissive, without passing through fluid phase 17, where it is detected by detector 33. Thus, in accordance with the method of the invention, the only light which is detected is from bound tracer 23 on the surface of the tube.

In a competitive assay as hereinabove described, the magnitude of the light emission is directly proportional to the quantity of bound tracer and therefore is inversely proportional to the quantity of analyte present in the fluid. The concentration of the analyte in the fluid may be determined by comparing the magnitude of light emission measured upon assay of the analyte with the emission measured upon assay of a range of known quantities of the analyte assayed under essentially identical conditions.

The method of the invention may be adapted to a solid phase sandwich assay. This type of assay is particularly useful for assay of a macromolecular analyte, as, for example, a protein. Any modification of solid phase sandwich assay may be used. For example, the antianalyte may be attached to the solid support in sufficient quantity to bind essentially all of the analyte through a first determinant on the analyte. The supported antianalyte may be incubated with the analyte, the light absorbing material and a tracer wherein the tracer comprises a labeled ligand specific for a second determinant on the analyte. The ligand may be an antigen, an antibody or a bound antigen-antibody complex. In a sandwich assay, the concentration of the analyte present in the fluid is directly proportional to the magnitude of light emission.

In accordance with another aspect of the invention, there is provided a reagent kit or package of materials for accomplishing an assay for an analyte in accordance with the method of the invention. The kit may include a solid support having attached thereto an antianalyte specific to the analyte, and may also include a component or an activator of a chemiluminescence source, a light absorbing material, and a tracer for the analyte having attached thereto a label. The kit may also include standards for the analyte, as, for example, one or more analyte samples of known concentration, or it may include other reagents or solutions, such as saline, buffers, or labeled or unlabeled specific antigens, antibodies or complexes thereof useful in carrying out the assay. The components of the kit may be supplied in separate containers, as, for example, vials, or two or more of the components may be combined in a single container.

The following examples are provided to further describe the invention, but are not in any way to be considered as limitative of the invention.

EXAMPLE I

Competition Immunoassay for Digoxin

A conventional commercially available kit for immunoassay of digoxin based on a peroxidative enzyme as the label may be used with the following modifications of the kit instructions.

A solution containing an unknown quantity of digoxin to be assayed and horseradish peroxidase-labeled digoxin is incubated in an antidigoxin coated test tube in accordance with the kit instructions. Without separation of the bound and free fractions, a buffered solution of luminol, hydrogen peroxide and Acid Yellow 29 is added, and light emitted by the luminescent reaction is measured by a luminometer. Since all light emitted consequent to reaction of peroxide and luminol with horseradish peroxidase on free tracer is absorbed by the Acid Yellow 29 in the solution and is not detected, all light detected by the luminometer is due to the bound tracer and is proportional to the concentration of digoxin in the unknown solution. The measured light is compared to the light emitted when the procedure is repeated with solutions containing known quantities of digoxin.

The concentration of the dye to be used is determined empirically such that it absorbs all of the light emitted by the peroxidase-hydrogen peroxideluminol reaction in the solution but not that emitted by the same reaction on the test tube wall. This dye concentration may be determined by performing the assay as described above in test tubes which have no anti-digoxin antibody coating. In this way, little or no luminescent reaction will take place on the test tube wall. The dye concentration is increased gradually to a point where no more light can be detected, and this concentration is used in the assay with the antibody-coated tubes.

EXAMPLE II

Sandwich Immunoassay for Human Chorionic Gonadotropin (hCG)

A commercially available kit for immunoassay of hCG based on a peroxidative enzyme may be used with the following modifications of the kit instructions. The washing step is omitted, a buffered solution of luminol, hydrogen peroxide and Acid Yellow 29 is added and the assay completed as in Example I. The only light emitted and measured is from the luminescent reaction on the tube wall giving a homogeneous assay.

Thus, in accordance with the invention, a method for solid phase CIA includes addition of a light absorbing material to the fluid phase of the assay system. The light absorbing material absorbs all the generated chemiluminescence except that emitted from bound tracer, whereby the emission from the bound tracer can be detected and measured in the presence of a large excess of free tracer. Separation of the bound and free fractions is thus avoided and the simplicity and convenience of a homogeneous assay is gained. The method is easily adaptable to all modifications of solid phase competitive and sandwich type assay systems. The invention includes a kit of assay materials which can be used for either manual or automated assay.

What is claimed is:

1. A method for determining an unknown quantity of an analyte in a fluid comprising:
   (a) preparing a mixture comprising an antianalyte attached to the surface of a tube, an analyte in a fluid, a light absorbing material, and a tracer for said analyte, said tracer including a chemiluminescent label;
   (b) causing binding involving immunologically specific pairs of said antianalyte, said analyte and said tracer whereby bound tracer is formed on the surface of said tube;
   (c) adding to said mixture a composite comprising an activator of a chemiluminescence source whereby chemiluminescence is induced;
   (d) measuring chemiluminescence associated with said bound tracer; and
   (e) determining the quantity of said analyte in said fluid by comparing the magnitude of said chemiluminescence with the magnitude of chemiluminescence established for a known quantity of the analyte.

2. The method in accordance with claim 1 wherein said analyte is selected from the group of analytes consisting of an antigen, a hapten and an antibody, and said antianalyte is selected from the group of antianalytes consisting of an antigen and an antibody.

3. The method in accordance with the claim 1 wherein said tracer further comprises said analyte having said label attached thereto, and wherein said tracer reacts specifically with said antianalyte.

4. The method in accordance with claim 3 wherein a limited amount of said antianalyte is attached to said support and said analyte and said tracer bind competitively to said antianalyte.

5. The method in accordance with claim 1 wherein said tracer is selected from the group of tracers consisting of an antigen, an antibody and a bound antigen-antibody complex having said label attached thereto and wherein said tracer reacts specifically with said analyte.

6. The method in accordance with claim 5 wherein substantially all of said analyte binds to said antianalyte and said tracer binds to said analyte.

7. The method in accordance with claim 1 wherein said analyte is in serum.

8. The method in accordance with claim 1 wherein said label is a component of said chemiluminescent source and reacts with said activator to induce said chemiluminescence.

9. The method in accordance with claim 8 wherein said light absorbing material has an absorption band which overlaps the emission band of said chemiluminescence.

10. The method in accordance with claim 1 wherein said label is an enzyme and said activator is a substrate for said enzyme.

11. The method in accordance with claim 10 wherein said enzyme is a peroxidative enzyme.

12. A method for determining an unknown quantity of an analyte in a fluid comprising:
    (a) preparing a mixture comprising an antianalyte attached to the surface of a tube, an analyte in a fluid, a light absorbing material and a tracer which includes a peroxidase;
    (b) causing binding involving immunologically specific pairs of said antianalyte, said analyte and said tracer whereby bound tracer is formed on the surface of said tube;
    (c) adding to said mixture a substrate for said peroxidase said substrate reacting with said peroxidase to cause chemiluminescence wherein substantially all of said chemiluminescence is absorbed by said light absorbing material except that caused by reaction of said substrate with said bound tracer;
    measuring chemiluminescence associated with bound tracer; and
    (e) determining the quantity of said analyte in said fluid by comparing the magnitude of said chemiluminescence with the magnitude of chemiluminescence established for a known quantity of the analyte.

13. A kit of materials for performing a chemiluminescence immunoassay for an unknown quantity of an analyte in a fluid comprising:
    (a) a tube having attached thereto an antianalyte specific to an analyte;
    (b) a light absorbing material; and
    (c) a tracer for said analyte, said tracer comprising a label, said label being a first component of a chemiluminescence source.

14. The kit in accordance with claim 13 further comprising a second component of a chemiluminescence source reactive with said label.

15. The kit in accordance with claim 13 further comprising at least one fluid containing analyte of known concentration.

16. The kit in accordance with claim 13 further comprising a fluid free of analyte.

17. The kit in accordance with claim 13 further comprising at least one other reagent selected from the group of reagents consisting of antigens, antibodies, complexes thereof, buffers and saline.

18. The kit in accordance with claim 13 further comprising one or more containers.

* * * * *